United States Patent [19]

Gergely et al.

[11] Patent Number: 5,759,575
[45] Date of Patent: Jun. 2, 1998

[54] EFFERVESCENT GRANULES AND PROCESS FOR THEIR PREPARATION

[75] Inventors: Gerhard Gergely, Gartengasse 8, A-1053, Wien; Thomas Gergely, Vienna; Irmgard Gergely, Vienna; Stephen Gergely, Vienna, all of Austria

[73] Assignee: Gerhard Gergely, Vienna, Austria

[21] Appl. No.: 605,019

[22] PCT Filed: Sep. 9, 1994

[86] PCT No.: PCT/EP94/03018

§ 371 Date: Mar. 26, 1996

§ 102(e) Date: Mar. 26, 1996

[87] PCT Pub. No.: WO95/07070

PCT Pub. Date: Mar. 16, 1995

[30] Foreign Application Priority Data

Sep. 9, 1993 [CH] Switzerland .................. 02700/93

[51] Int. Cl.⁶ .................. A61K 9/16; A61K 9/46
[52] U.S. Cl. .................. 424/466; 424/489; 514/770; 514/784
[58] Field of Search .................. 424/466, 489; 514/770, 784

[56] References Cited

U.S. PATENT DOCUMENTS

| 4,783,331 | 11/1988 | Alexander et al. ............ 424/44 |
| 4,867,942 | 9/1989 | Gergely et al. ............ 424/466 |
| 5,401,524 | 3/1995 | Burkes et al. ............ 426/590 |

FOREIGN PATENT DOCUMENTS

| 525 388 | 2/1993 | European Pat. Off. . |
| 2 552 308 | 3/1985 | France . |
| 2552308 | 3/1985 | France . |
| WO 94/00107 | 1/1994 | WIPO . |

Primary Examiner—James M. Spear
Attorney, Agent, or Firm—Oliff & Berridge, PLC

[57] ABSTRACT

An effervescent granulated material for a pharmaceutical preparation contains calcium carbonate and citric acid. From 5-20 parts by weight of the total acid provided for the reaction with the calcium carbonate is replaced by at least one of malic acid, gluconic acid, lactic acid, and their salts. Citric acid and calcium carbonate are granulated with a partial reaction, and in each case at least part of the compound partially replacing the citric acid is granulated in solid, powdered form together with the citric acid and the calcium carbonate and/or dissolved in a granulation liquid or buffer solution.

15 Claims, 1 Drawing Sheet

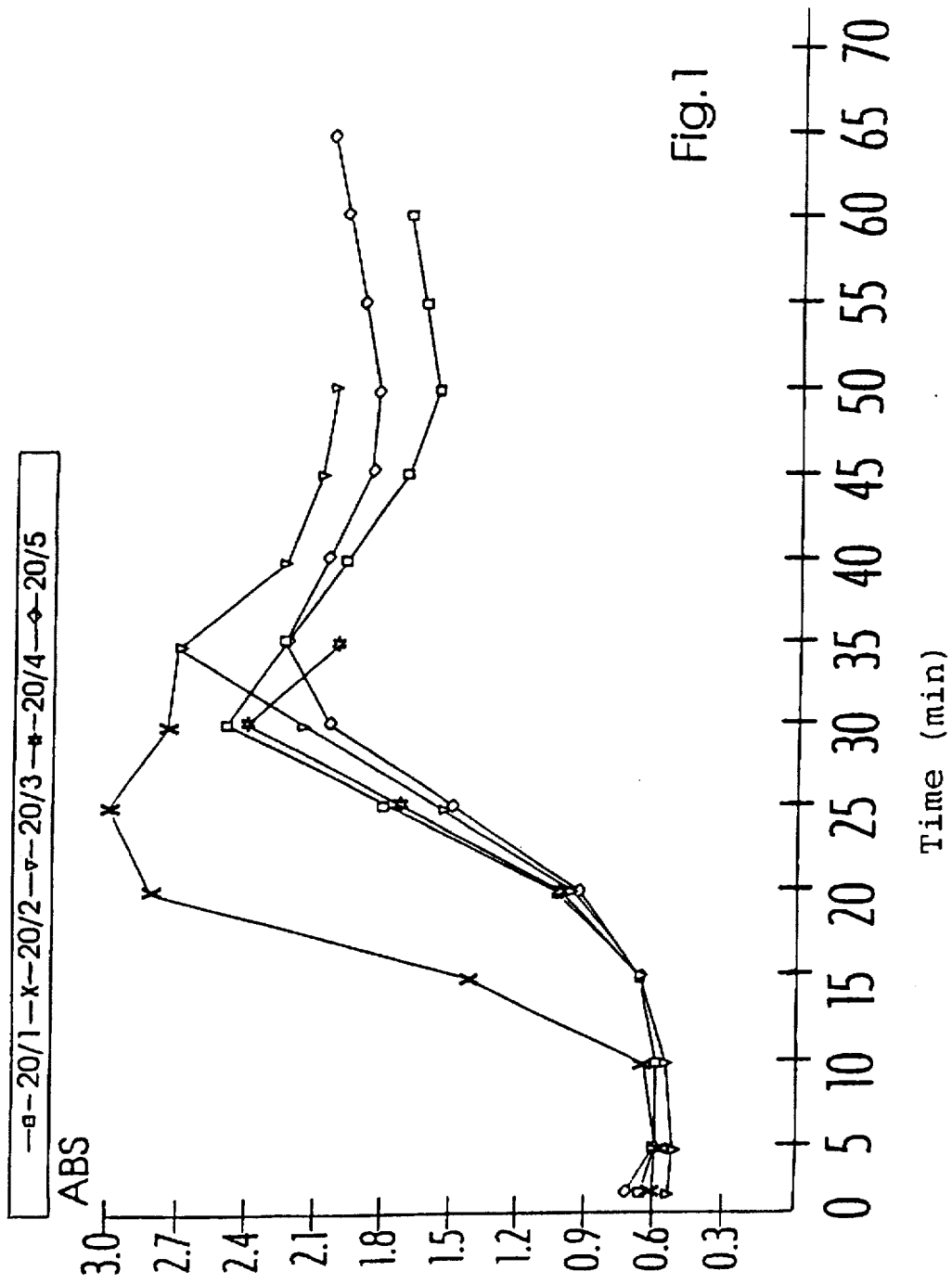

EFFERVESCENT GRANULES AND PROCESS FOR THEIR PREPARATION

This application is a 371 of PCT/EP94/03018 filed Sep. 9, 1994.

The invention relates to effervescent granules for the preparation of a pharmaceutical formulation containing citric acid and calcium carbonate, and a process for the preparation of said granules. The preparation of such products is described, for example, in FR-A-2 552 308 and U.S. Pat. No. 4,867,942. However, high-dose effervescent calcium tablets which contain 2.5 g of calcium carbonate (equivalent to 1000 mg of calcium) and 4–4.5 g of citric acid show that effervescent solutions containing a relatively high concentration of calcium ions dissolved in 150 or 200 ml of water tend to form precipitates of insoluble tricalcium citrate on prolonged standing of the ready-to-drink solution. The time up to precipitation of the tricalcium citrate and the amount of the precipitate are dependent on the concentration of the calcium ions and citric acid in the ready-to-drink solution. However, since the consumer prefers to dissolve a tablet in 150 to not more than 200 ml of water, and very often the solution is not drunk immediately, this phenomenon is always a point of criticism, and all the more so since even effervescent tablets which contain only 500 mg of calcium ions in 150 ml of water exhibit such a precipitation, even if with a substantial delay, i.e. of up to about 1 hour.

WO 94/00107 has already proposed delaying this undesired effect by replacing a significant part (25 to 73%) of the citric acid with malic acid, and optionally by various salts. They interfere with the formation of pure tricalcium citrate—evidently by partial binding of the calcium carbonate and by formation of mixed salts—so that it takes substantially longer for the law of mass action to apply.

However, such large amounts of malic acid make the product considerably more expensive and restrict the use essentially to powder mixtures which can be compressed to give tablets only by special measures. The granulation properties of the material are in fact seriously impaired by these large additions: the material becomes very pasty. In addition, such tablets dissolve too slowly and residue formation may occur under certain circumstances during dissolution, since the conversion to, for example, calcium malate takes place too slowly during the dissolution process; this then results in residues of unreacted calcium carbonate.

The addition of the delta-lactone of gluconic acid, proposed in FR-A-2 552 308 (Example 4), also exhibits the effect according to the invention much too weakly, since said lactone liberates gluconic acid only in the presence of relatively large amounts of water, so that the advantages expected for the preparation of the effervescent granules (see below) are not achieved.

These problems are now solved in a surprising manner for the first time by replacing 5 to 20, preferably 10 to 15, percent by weight of the citric acid with at least one foreign acid which, apart from malic acid, may also be gluconic acid or lactic acid. Other acids are therefore less advantageous because tartaric acid forms an insoluble calcium tartrate; adipic acid and ascorbic acid exhibit the desired effect only weakly, if at all, and adipic acid itself is moreover only slightly soluble. On the other hand, the stated lower limit is also important: the claimed acids too exhibit the desired effect only too weakly, if at all, when they are used in amounts of only less than 5 percent by weight.

During many attempts to solve the problem, it was found that replacing as little as 100 mg of citric acid with malic acid in an effervescent tablet with 1000 mg of calcium delays the precipitation time in 125 ml of water: a batch with a very strong tendency towards precipitation was improved from an original value of 7 min by 30% to 9.5 min and, with the addition of 200 mg, by 50% to 11 min. The turbidity was tested photometrically as absorbance at 480 nm at an identical value in order to obtain objective parameters.

BRIEF DESCRIPTION OF THE DRAWING

Replacing only 5–15% by weight of the citric acid with malic acid increases the precipitation time almost by a factor of 2, but at least by 50% (cf. FIG. 1) without changing the pH of the solution. It is furthermore found that the foreign acids have the same effect regardless of whether incorporation in the granules or dry mixing is carried out, although granulation is preferred, not least for process engineering reasons.

Further acids which have proved advantageous are gluconic acid and lactic acid, and the latter may simultaneously be used as granulating solution.

For the preparation of the effervescent granules, too, the addition of a second acid has proved advantageous with regard to the precipitation. In the preparation of effervescent granules of calcium carbonate and possible alkali metal carbonates and bicarbonates with citric acid, large amounts of solutions are required in order to obtain a partial reaction of calcium carbonate and citric acid; moreover, elevated temperatures additionally have an effect during the granulation or during the drying; consequently, a small amount of tricalcium citrate is formed in some cases during the preparation of the granules themselves and appears as an insoluble residue in the glass immediately after dissolution of the granules or of the tablet.

The addition of foreign acids is therefore advantageous during granulation because this suppresses the formation of tricalcium citrate during granulation and drying and substantially simplifies the production of such an effervescent tablet without special precautions.

Furthermore, the preparation of granules in the presence of the foreign acid is improved by virtue of the fact that, on wetting of the solutions, mutual dissolution of citric acid and foreign acid, i.e. for example malic acid, occurs, resulting in a melting point depression of both acids, which is an extremely good tabletting aid. This also permits simpler production of the product, so that there is greater independence of the particle structures and it is possible to use powdered citric acid or a mixture of crystalline citric acid and powdered malic acid without tricalcium citrate being formed as a result of the increased contact of calcium carbonate with citric acid during the granulation reaction. As a result of the melting point depression mentioned and mutual penetration of the solutions, granules which are extremely elastic and easy to compress are obtained.

The granulation can be carried out with polar solvents and polar solvent mixtures, and of course the use of buffer solutions is also advantageous for preventing excessively strong reactions.

As already mentioned, it is also possible to carry out granulation with a solution of, for example, malic acid or lactic acid in polar solvents, the effects of the improved granulation behaviour, of the prevention of the formation of tricalcium citrate during the preparation and also of the delay of precipitation in the glass being retained.

The fluorine compounds used in osteoporosis treatment, such as, for example, sodium fluoride, sodium monofluorophosphate, zinc fluorophosphate, etc., can also be added to these granules or incorporated in these granules.

3

Fluoroapatites may also be incorporated, the apatites, owing to their slight solubility in the milled state, being suspended in the resulting solution and being kept in suspension.

EXAMPLE 1

(FIG. 1, Batch 20/5):

Replacement of 14% of the total acid with powdered malic acid and granulation with water/ethanol, the citric acid being used exclusively in powdered form:

2500 parts by weight of calcium carbonate are mixed with 3700 parts by weight of powdered citric acid and 600 parts by weight of powdered malic acid and granulated at 45° C. with 200 parts by weight of 70% ethanol for 10 min with reaction. Thereafter, drying is carried out by means of reduced pressure at a temperature of 60° C. and the product is compressed to give tablets.

The time from the dissolution of the tablet to the occurrence of turbidity due to tricalcium citrate was 35 min and was thus almost twice as long as that of a comparative tablet without malic acid.

EXAMPLE 2

(Batch 20/1 in FIG. 1):

Replacement of 19% of the total acid with malic acid; use of citric acid in crystalline and powdered form, granulation with water:

2500 parts by weight of calcium carbonate are mixed with 2700 parts by weight of crystalline citric acid, 800 parts by weight of powdered citric acid and 800 parts by weight of malic acid, heated to 45° C., granulated with 120 parts by weight of water and finally dried. The granules are still just readily compressible.

The precipitation time was 30 min in comparison with 15 min for the product without malic acid; it is thus possible to achieve an increase of 100%.

EXAMPLE 3

(Batch 20/4 of FIG. 1):

Replacement of 9% of the total acid with malic acid: similarly to Example 2, only 400 parts by weight of the total acid can be replaced with malic acid; the mixture is then granulated in two stages with a buffer solution (for example, a prereaction solution corresponding to U.S. Pat. No. 4,867, 942), which is prepared as follows: 130 parts by weight of citric acid and 27 parts by weight of calcium carbonate are dissolved in 180 parts by weight of water. In FIG. 1, the product 20/4 shows an increase in precipitation time from 18 to almost 30 min at the absorbance of 2.1 in comparison with the product without malic acid (Batch 20/2).

EXAMPLE 4

(Batch 20/3 in FIG. 1):

The procedure described in Example 3 can be adopted, the total 400 parts by weight of the malic acid being dissolved in the granulation liquid comprising 300 parts by weight of an ethanol/water mixture (1:1) and acting as a buffer solution. With regard to the time until the beginning of formation of the tricalcium citrate, the end product shows the same behaviour as that of Example 3.

EXAMPLE 5

The procedure is as in Example 4, except that, instead of being prepared from malic acid, the buffer solution is prepared from 250 parts by weight of gluconic acid or lactic acid (calculated as dry substance) by dilution with 100 ml of water. With regard to the time until the beginning of formation of tricalcium citrate, the end product shows the same behaviour as that of Example 4.

4

We claim:

1. Effervescent granules for the preparation of a pharmaceutical formulation comprising:

calcium carbonate;

citric acid; and a further, solid, edible, organic acid selected from the group consisting of malic acid, gluconic acid, lactic acid and salts thereof, wherein 5–20% by weight of the total amount of citric acid intended for reaction with the calcium carbonate is replaced with the further, solid, edible, organic acid.

2. Effervescent granules according to claim 1, characterized in that the organic acids are covered by at least a part of the calcium carbonate and are present in a form partially reacted and granulated with it.

3. Effervescent granules for the preparation of a pharmaceutical formulation comprising:

calcium carbonate;

citric acid;

a further, solid, edible, organic acid selected from the group consisting of malic acid, gluconic acid, lactic acid and salts thereof; and a pharmaceutically effective amount of at least one fluorine compound, wherein 5–20% by weight of the total amount of citric acid intended for reaction with the calcium carbonate is replaced with the further, solid, edible, organic acid.

4. A process for the preparation of effervescent granules comprising:

calcium carbonate;

citric acid; and a further, solid, edible, organic acid selected from the group consisting of malic acid, gluconic acid, lactic acid and salts thereof, wherein 5–20% by weight of the total amount of citric acid intended for reaction with the calcium carbonate is replaced with the further, solid, edible, organic acid;

the process comprising granulating citric acid and calcium carbonate with a partial reaction, wherein at least part of the further, solid, edible, organic acid that replaces the citric acid is mixed in a solid powdered form with the citric acid and the calcium carbonate and the substances are granulated together with moistening.

5. A process for the preparation of effervescent granules comprising:

calcium carbonate;

citric acid; and a further, solid, edible, organic acid selected from the group consisting of malic acid, gluconic acid, lactic acid and salts thereof, wherein 5–20% by weight of the total amount of citric acid intended for reaction with the calcium carbonate is replaced with the further, solid, edible, organic acid;

the process comprising granulating citric acid and calcium carbonate with a partial reaction, wherein at least part of the further, solid, edible, organic acid that partially replaces the citric acid is dissolved in a granulation liquid.

6. The effervescent granules according to claim 3, wherein 9–19% by weight of the total amount of citric acid intended for reaction with a calcium carbonate is replaced with a further, solid, edible, organic acid.

7. The effervescent granules according to claim 1, wherein 10–15% by weight of the total amount of citric acid intended for reaction with the calcium carbonate is replaced with the further, solid, edible, organic acid.

8. The effervescent granules according to claim 4, wherein 9–19% by weight of the total amount of citric acid intended for reaction with a calcium carbonate is replaced with a further, solid, edible, organic acid.

9. The effervescent granules according to claim 5, wherein 9–19% by weight of the total amount of citric acid intended for reaction with a calcium carbonate is replaced with a further, solid, edible, organic acid.

10. Effervescent granules as claimed in claim 1, wherein said granules consist essentially of:

calcium carbonate;

citric acid; and a further, solid, edible, organic acid selected from the group consisting of malic acid, gluconic acid, lactic acid and salts thereof.

11. The process according to claim 5, wherein the granulation liquid is a buffer solution.

12. The effervescent granules according to claim 3, wherein 10–15% by weight of the total amount of citric acid intended for reaction with the calcium carbonate is replaced with a further, solid, edible, organic acid.

13. The effervescent granules according to claim 4, wherein 10–15% by weight of the total amount of citric acid intended for reaction with the calcium carbonate is replaced with a further, solid, edible, organic acid.

14. The effervescent granules according to claim 5, wherein 10–15% by weight of the total amount of citric acid intended for reaction with the calcium carbonate is replaced with a further, solid, edible, organic acid.

15. The effervescent granules according to claim 1, wherein 9–19% by weight of the total amount of citric acid intended for reaction with a calcium carbonate is replaced with a further, solid, edible, organic acid.

* * * * *

UNITED STATES PATENT AND TRADEMARK OFFICE
CERTIFICATE OF CORRECTION

PATENT NO. : 5,759,575
DATED : June 2, 1998
INVENTOR(S) : Gerhard GERGELY; Thomas GERGELY; Irmgard GERGELY; Stefan GERGELY It is certified that error appears in the above-indentified patent and that said Letters Patent is hereby corrected as shown below:

On the title page, item
    [75] Inventors: Gerhard Gergely, Gartengasse 8.
        A-1053. Wien; Thomas Gergely.
        Vienna; Irmgard Gergely. Vienna;
        Stefan Gergely. Vienna. all of Austria Signed and Sealed this Seventeenth Day of November, 1998

Attest:

BRUCE LEHMAN

*Attesting Officer*   *Commissioner of Patents and Trademarks*